United States Patent [19]

Milgram

[11] Patent Number: 5,225,446
[45] Date of Patent: Jul. 6, 1993

[54] USE OF 1-DEPRENYL FOR RETENTION OF SPECIFIC PHYSIOLOGICAL FUNCTIONS

[75] Inventor: Norton W. Milgram, Scarborough, Canada

[73] Assignee: Deprenyl Animal Health, Inc., Overland Park, Kans.

[21] Appl. No.: 913,298

[22] Filed: Jul. 14, 1992

Related U.S. Application Data

[62] Division of Ser. No. 576,011, Aug. 31, 1990, Pat. No. 5,151,449.

[51] Int. Cl.$^5$ .............................................. A61K 35/135
[52] U.S. Cl. .................................... 514/654; 514/646; 514/649; 514/909
[58] Field of Search ................ 514/654, 909, 649, 646

[56] References Cited

U.S. PATENT DOCUMENTS

| | | | |
|---|---|---|---|
| 4,564,706 | 1/1986 | Ecsery | 564/376 |
| 4,871,550 | 10/1989 | Millman | 424/601 |
| 4,913,891 | 4/1990 | Fowler et al. | 424/11 |
| 4,960,797 | 10/1990 | Ecsery et al. | 514/654 |
| 5,151,449 | 9/1992 | Milgram | 514/654 |

*Primary Examiner*—Frederick E. Waddell
*Assistant Examiner*—T. J. Criares
*Attorney, Agent, or Firm*—Zarley, McKee, Thomte, Voorhees & Sease

[57] ABSTRACT

1-Deprenyl and pharmaceutically acceptable analog forms thereof are used at specific dosage levels and frequency of dosage to slow the normal age dependent deterioration of renal function, to provide increased exploratory behavior level of activity at any given age and in order to retard age deterioration of cognitive abilities, especially spatial learning ability. The treatment can be especially useful for mammals, for examples pets such as dogs and cats.

7 Claims, No Drawings

USE OF l-DEPRENYL FOR RETENTION OF SPECIFIC PHYSIOLOGICAL FUNCTIONS

This is a divisional of copending application Ser. No. 07/576,011 filed on Aug. 31, 1990, now U.S. Pat. No. 5,151,449.

BACKGROUND OF THE INVENTION l-Deprenyl is a selective monoamine oxidase B (MAO-B) inhibitor, which is widely used as an adjunct in the treatment of Parkinson's disease. While it's most common usage is for the treatment of Parkinson's disease, l-deprenyl was originally developed as an antidepressant agent. Recent testing has indicated that l-deprenyl may have some effect on increasing sexual response in aging animals, and also may have some effect, at least in rats in increasing the natural life span. However, to date l-deprenyl has only been medically approved by regulatory agencies for use for treatment of Parkinson's disease.

The search for new lines of medication to improve the quality of life in senescence ever continues. This becomes especially important in modern-day society, especially in developed countries, where the proportion of citizens over 65 years of age continues to increase. In sum, the quality of life has become increasingly important in older years, as people continue to experience longer life expectancy.

There is, therefore, a continuing and real need for the development of medications which retard the normal deterioration of certain physiological functions.

It is a primary objective of the present invention to develop a dosage regimen for the use of l-deprenyl to retard deterioration of normal renal function with age, to retard deterioration of cognitive abilities during advanced aging, and to retard the deterioration in the natural tendency for curious or exploratory behavior in aged mammals, such as pets like dogs and cats.

While l-deprenyl is a known compound, it has never before been used at any level to retard physiological effects of age deterioration on certain organs, such as kidneys, nor to retard cognitive ability deterioration with age.

Like most drugs, l-deprenyl can have diverse physiological effects which are completely dependent upon the dose administered. In accordance with the present invention, l-deprenyl can be used for successful methods of treatment to provide the desired physiological effects enumerated herein, providing that it is used at the dosage levels mentioned herein and providing it is administered at the periodic intervals and for the time spans mentioned herein. Obviously, when different dosages and levels of treatment are used, the results expressed herein may not be achieved. In fact, at higher doses, adverse behavioral effects may be encountered.

SUMMARY OF THE INVENTION

The present invention relates to the process of using a known compound, l-deprenyl, for new uses. In particular, at the dosage levels described herein, providing that the dosage is used for at least the periods of time expressed herein, there is an observed retardation of normal age dependent deterioration of renal function and an observed retardation of normal degeneration of cognitive abilities, including spatial learning ability. Further, the age-dependent weight loss may also be avoided. The treatment is especially useful for domesticated pets, like dogs and cats, as they increase in age, but would be expected to have utility in any mammal species.

DETAILED DESCRIPTION OF THE INVENTION

As earlier stated, the compound that is useful for the method or protocol of the present invention is a known compound, l-deprenyl. l-Deprenyl has the formula (-)-N-$\alpha$-dimethyl-N-2-propynylbenzene-ethanamine. It can be illustrated by the following graphic formula:

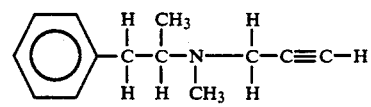

l-Deprenyl also is at times referred to as L-deprenyl to illustrate that it is a levorotary isomer which is the active form for treatment of Parkinson's disease. Typically, it is provided in a pharmaceutically acceptable salt form thereof such as the hydrochloride salt.

As used here, pharmaceutically acceptable salt form thereof, means the following. Acceptable for use in the pharmaceutical or veterinary art, being nontoxic or otherwise not pharmaceutically or veterinary unacceptable. "Acceptable salt form thereof" means salts formed with inorganic acids such as hydrochloric acid, hydrobromic acid, sulfuric acid, nitric acid, phosphoric acid, and the like, and as well organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, etc.

Administration of the therapeutically active compound l-deprenyl to achieve physiological results of the present invention can be via any of the accepted modes of administration for systemically active substances. These methods include oral, parenteral, and otherwise systemic, aerosol, and topical forms, as well as sustained release systems, etc.

The compositions of the present invention may be any of those known in the pharmaceutical and veterinary arts which are suitable for the method of administration and dosage required in any particular circumstance. In the case of both pharmaceutical and veterinary applications, such compositions may include tablets, pills, capsules, powders, aerosols, suppositories, skin patches, parenterals, and oral liquids including oil aqueous suspensions, solutions and emulsions. It may include long acting injectables and sustained release devices.

When the dosage is in solid form, solid pharmaceutical carriers such as starch, sugar, talc, mannitol, povidone, magnesium stearate, and the like may be used to form powders. Lactose and mannose are the preferred solid carrier. The powders may be used as such for direct administration to a patient or, instead, the powders may be added to suitable foods and liquids, including water, to facilitate administration.

The powders also may be used to make tablets, or to fill gelatin capsules. Suitable lubricants like magnesium stearate, binders such as gelatin, and disintegrating agents like sodium carbonate in combination with citric acid may be used to form the tablets.

Unit dosage forms such as tablets and capsules may contain any suitable predetermined amount of l-deprenyl, advisably as a nontoxic acid addition salt, and may be administered one or more at a time at regular intervals as later described. Such unit dosage forms, however, should with a broad range guideline contain a concentration of 0.1% to 10% by weight of one or more forms of the active 1-deprenyl.

A typical tablet may have the composition:

|   |   | Mg. |
|---|---|---|
| 1. | 1-Deprenyl | 10.0 |
| 2. | Mannitol | 100 |
| 3. | Stearic Acid | 3 |

A granulation is made from the mannitol. The other ingredients are added to the dry granulation and then the tablets are punched.

Another tablet may have the composition:

|   |   | Mg. |
|---|---|---|
| 1. | 1-Deprenyl | 10 |
| 2. | Starch U.S.P. | 57 |
| 3. | Lactose U.S.P. | 73 |
| 4. | Talc U.S.P. | 9 |
| 5. | Stearic acid | 6 |

Powders 1, 2 and 3 are slugged, then granulated, mixed with 4 and 5, and tableted.

Capsules may be prepared by filling No. 3 hard gelatin capsules with the following ingredients, thoroughly mixed:

|   |   | Mg. |
|---|---|---|
| 1. | 1-Deprenyl | 5 |
| 2. | Lactose U.S.P. | 200 |
| 3. | Starch U.S.P. | 16 |
| 4. | Talc U.S.P. | 8 |

As earlier expressed, physiological functions effected by the treatment herein with 1-deprenyl are necessarily dosage dependent. Put another way, like most drugs, 1-deprenyl has diverse physiological effects depending upon the dose administered. Unless the dose administered is within the levels set forth herein, the desired effects on renal function, weight retention, and cognitive processes are not achieved without adverse effects.

While the tests later described herein are only provided for testing of male Fischer rats purchased from Harlan Spraugue Dawley, the tests are a fair generalizations for mammals. And therefore, the term mammal as used herein includes without limitation humans and domesticated animals such as cattle, horses, swine, sheep, dogs, cats, goats and the like. The tests are particularly illustrative for domesticated pets such as dogs and cats. The treatment may even work for birds or fish.

Renal function and cognitive abilities for dogs and cats are especially important as they age. Among other reasons, this is in part because humans form quick and strong bonds with their domesticated pets, and these strong bonds increase the desire to keep the animal alive for many years, often well beyond the peak years of efficient organ function and peak cognitive abilities. This may cause many problems if the animal is a house pet.

Needless to say, the natural enjoyment of these pets would be significantly increased in their older age if one could retard the decrease in physiological functions and cognitive processes. For example, it often happens that older dogs and cats increasingly lose their renal function. Moreover, as dogs and cats get older, they usually have decreased cognitive functions, especially a decrease in spatial learning ability and their natural exploratory behavior, i.e. level of curiosity. These natural changes alter the animal's personality such that the human owner has less enjoyment from the animal.

In accordance with the present invention, it has been illustrated the renal function deterioration can be retarded, and in fact exploratory behavior can be increased in older animals, and cognitive ability deterioration can be retarded, especially spatial learning ability if the animal is treated periodically with small but therapeutically effective doses of 1-deprenyl. Additionally, age-dependent weight loss can be prevented.

As hereinafter explained, the dosage regimen to achieve these desirable results differs considerably from the dosage regimen used in treating Parkinson's disease. At the highest doses recommended for uses disclosed herein, the levels are less than one-half the amount used for treating Parkinson's disease. In particular, the dosage regimen of the present invention shows usage at levels from about 0.01 mg/kg of body weight up to about 1.0 mg/kg of body weight from one to seven times weekly, but preferably on alternate days. Most preferably the dosage level is 0.05-0.5 mg/kg of body weight given twice weekly, starting in middle age. Of course it would be known to those in the art that sustained release systems can be used to provide less frequent dosing to achieve the required dosage level.

It is not known precisely why the use of 1-deprenyl at the dosage levels and periodicity expressed herein achieves these results. While not wishing to be bound by any theory of operation of the present process, it is believed that rather than central processing in the brain there may be a direct effect on the kidney. The effect may be hypotensive. As explained in the examples below, analysis of serum chemistry suggests that the 1-deprenyl treatment may have a direct effect on kidney function. With regard to the cognitive processes, it is simply not known by what mechanism the compound works, except to say that it is critically important that the dosage be at levels expressed herein rather than in Parkinson's disease levels, otherwise adverse effects may be achieved, particularly in dogs.

In the tests and examples reported hereinafter, differences in renal function between control and 1-deprenyl treated animals was measured by an examination of blood chemistry and in particular the level of blood urea nitrogen (BUN), which is a measure of waste product which is cleared from the body by the kidneys. High levels are indicative of ineffective renal function, and low levels are correspondingly an indication of proper renal function.

Tests of cognitive ability, i.e. memory and response acquisition, were measured in a water maze test. The particular animals were placed in a water maze, as described below and given 90 seconds to swim and locate a platform and climb upon it and escape from the water, for which these animals show a natural aversion. Repeat testing continued until the animals learned that once placed in the water they could swim to the platform and easily prevent drowning. Memory was measured by the ability of the rat to retain this learned behavior five days following the last maze test. In particular, five days after the maze test, the rats were placed in the water maze again, with the platform removed. As a retention measure, time spent in the region of the maze where the platform would normally have been was recorded. The same procedure was repeated twice more each time with the platform in a new location. By doing so, the animals' ability to profit from its previous experience was tested.

During the late stages of aging, rats show a progressive decrease in body mass, and an examination of individual data indicates that decreased body weights proved to be a reliable predictor of death. In the test data of the rats studied in the examples, body weights of the controls and the 1-deprenyl treated rats were recorded. It was uniformly observed that normal age dependent body mass loss was retarded in the 1-deprenyl treated group and that this was not associated with dietary differences. In sum, at advanced stages of aging, the surviving 1-deprenyl rats were significantly heavier than the surviving controls.

EXAMPLES

In the examples below, male Fischer rats from Harlan Sprague Dawley were used. The animals were obtained at 21–23 months of age. They were allowed free access to food and water, and were weighed on every other day.

1-Deprenyl treatment was started when the animals were between 24 and 25 months of age. The drug was administered subcutaneously at a dose of 0.25 mg/kg on alternate days until the animal either died or was removed from the experiments. The deprenyl was dissolved in a solution of saline.

Serum analysis was done on the animals on two occasions, at the start of the experiment, and again after 3 months of treatment. The blood samples were taken intraorbitally, which could only be done on anesthetized animals. As an anesthetic, a mixture of equivalent volumes of ketamine and atravin were used because the combination has a low toxicity, and short duration of effect in young rats. In the baseline test, a dose of 0.2 ml was used. However, this induced a much deeper and longer lasting period of anesthesia than was desired and the dosage was subsequently reduced to 0.08 ml for the three month test.

The samples were immediately sent to Vita-Tech Canada, where biochemical assays were done for: glucose, creatinine, bilirubin (total), blood urea nitrogen (BUN), SGOT, SGPT, total protein and albumin. For analysis of hematology, measurements were taken of hemoglobin, hematocrit, RBC counts, WBC counts, MCH, neutrophils, lymphocytes, monocytes, eosinophils, Basophils, and nRBC. A double blind procedure was followed in collection and analysis of serum biochemistry and hematology. The results of the serum analysis are summarized in Table 1. The only significant difference between the controls and 1-deprenyl group at three months was in the measure of (BUN). The comparisons for creatinine ($p = 0.129$), albumin ($p = 0.117$) and A/G ration ($p = 0.151$) were close to the significance level, while there were clearly no differences in bilirubin ($p = 0.826$), SGOT ($p = 0.990$) and SGPT ($p = 0.667$). Table 1 also shows the correlation between each of the measures and survival. The levels of BUN, SGOT and bilirubin all correlated significantly.

TABLE 1

Effect of l-deprenyl on Measures of Serum Chemistry

| Measure | Control N = 24 | BASELINE Deprenyl N = 29 | Correlation with survival | Control N = 22 | 3 MONTHS Deprenyl N = 23 | Correlation with survival |
|---|---|---|---|---|---|---|
| A/G Ratio | .97 ± .02 | .97 ± .03 | .10 | .75 ± .02 | .81 ± .04 | .14 |
| Albumin g/L | 29.92 ± .71 | 29.76 ± .89 | .13 | 24.0 ± .73 | 25.62 ± .74 | .51** |
| Bilirubin umol/L | 3.05 ± .25 | 2.93 ± .24 | −.26 | 4.19 ± .41 | 4.43 ± .98 | −.35 |
| BUN mmol/L | 8.45 ± .29 | 8.18 ± .22 | −.12 | 14.02 ± 1.61 | 9.95 ± .45[1] | −.51** |
| Creatinine umol/L | 73.13 ± 1.97 | 70.93 ± 1.61 | −.01 | 85.28 ± 5.82 | 75.52 ± 2.68 | −.13 |
| Glucose mmol/L | 7.73 ± 1.03 | 7.19 ± .73 | .11 | 7.87 ± .76 | 8.50 ± .62 | .38* |
| Total Protein g/L | 60.58 ± 4.93 | 60.31 ± .95 | .17 | 56.73 ± 1.47 | 57.69 ± .93 | .57** |
| SGOT U/L | 108.96 ± 8.43 | 121.41 ± 1.10 | .07 | 135.32 ± 17.10 | 135.79 ± 32.00 | .47* |
| SGPT U/L | 63.96 ± 4.72 | 64.52 ± 4.56 | .05 | 60.04 ± 6.03 | 67.04 ± 14.68 | .45* |

Scores represent means ± SEM. Correlations are with days survival from the start of the experiment.
[1] significantly different from controls using a two-tailed test ($P = .017$)
*significant at .01 level
**significant at the .001 level The blood chemistry data was informative, and provide a possible explanation as to why animals treated with 1-deprenyl survived longer than the controls. At 26 months, there was a significant difference in the measure of BUN, with the deprenyl group having a lower score than the controls. BUN is a measure of a waste product which is cleared from the body by the kidneys. High levels are therefore indicative of ineffective renal function. Differences in renal function between the deprenyl group and the control group were also indicated by the differences in amounts of creatinine (deprenyl lower than controls), although the size of the differences did not achieve statistical significance.

In a comparison between 23 and 26 month animals, it was found that both BUN and creatinine were significantly higher in the 26 month test. These results were not unexpected, since it is known that the rat, like other mammals, shows marked deterioration of renal function with advanced age. The significant drug effect at 26 months therefore is indicative of 1-deprenyl treatment providing protection of renal function. That such protection is associated with survival is further indicated by the significant correlation between BUN measure and days of survival in the 26 month group.

The absence of differences between the deprenyl and controls on the other biochemical measures may be indicative of deprenyl affecting the kidneys to a greater extent than it does other peripheral organs, or that the rats were too old at the star of treatment.

The water maze consisted of a circular chamber filled with water to a depth which just covered the surface of a transparent platform, 17.75 cm in height. At the start of each session, the rat was placed in the tank facing the outer surface at a randomly determined point, approximately 1 meter from the center of the platform. Animals were given 90 seconds to locate and climb upon the platform. The animal was removed from the platform after 30 seconds. A correction procedure was used. If the animal did not find the platform, it was gently guided to it at the end of the trial, and removed after 30 seconds. Testing continued until either the criterion of escaping onto the platform within 25 seconds on four out of five consecutive trials was achieved or 30 trials had been completed. A maximum of ten trials were given each day, with an interval of 30 minutes between each trials. Every trial was also videotaped.

Retention was tested five days following the last acquisition trial by placing the rats in the maze for three 90 second trials with the platform removed. As a retention measure, the time was recorded that was spent in the region of the maze where the platform had earlier been located. A second set of acquisition trials were then given using same procedures followed during the original training, except that the platform was moved to another location. Following acquisition and subsequent retention trials, the animals received a third set of trials—again with the platform at another position. Thus, each animal was tested for both acquisition and retention on three separate occasions.

Changes in cognitive abilities of animals treated with l-deprenyl and control were measured in the water maze test, earlier described.

Water maze acquisition was tested in 16 animals (8 deprenyl and 8 control) at 26 months. The deprenyl group were tested while in their third month of drug treatment. An additional three animals started the testing, but were dropped because of inability to swim acceptably. At 29 months, 9 animals (5 deprenyl and 4 controls) were tested on the water maze. The deprenyl animals were in their sixth month of drug treatment. Five additional rats were unable to swim or were moribund at the start of testing.

Analysis of water maze acquisition was based upon the number of trials required to reach criterion. A maximum score of 33 was assigned if an animal did not learn the task within the three day test period. The results are summarized in Table 2. An analysis of variance with age and session as main effects indicated a significant age effect reflecting slower learning in the older animals ($F(2,58)=10.5$, $p=0.00$), and a significant session effect reflected improvement in learning over repeated testing ($F(2,58)=11.12$, $p=0.00$). There was also a tendency for the younger animals to show greater improvement, although the age by session interaction was not significant ($F(6,58)=1.64$, $p=0.152$).

To test for drug effect in acquisition, the 26 and 29 month animals were compared with a three way analysis of variance with age, group and session as main effects. There were significant main effects for age ($F(1.21)=4,62$, p-0.143) and session ($F(2,42)=2.55$, $p=0.29$). The group effect was not significant, the age by group interaction was highly significant ($F(2,42)=12.2$, $p=0.002$) As indicated in Table 2, this finding is attributable to the deprenyl group performing poorly when tested at 26 months, and better than the controls when tested at 28–29 months.

The results of the retention tests, on the other hand, did not reveal any consistent effects of group or age.

TABLE 2

Mean Trials to criterion (± SE) in water maze as a function of age, treatment with L-deprenyl and previous trials

| Age (month) | Group | N | Test 1 | Test 2 | Test 3 |
|---|---|---|---|---|---|
| 7 | Control | 9 | 15.67 ± 1.91 | 10.67 ± 3.18 | 9.33 ± 2.03 |
| 23 | Control | 12 | 18.50 ± 2.49 | 12.25 ± 2.83 | 5.67 ± .86 |
| 26 | Control | 8 | 17.88 ± 3.86 | 15.87 ± 1.87 | 8.00 ± .96 |
|  | Deprenyl | 8 | 22.63 ± 3.54 | 22.38 ± 3.85 | 21.75 ± 3.58 |
| 29 | Control | 4 | 31.00 ± 0.71 | 26.25 ± 5.81 | 29.00 ± 4.67 |
|  | Deprenyl | 4 | 25.40 ± 2.69 | 17.20 ± 4.22 | 13.80 ± 5.07 |

The control rats showed better acquisition at 26 months than the deprenyl group, while at 29 months the results were reversed—with the deprenyl group showing superior learning. The poor acquisition seen in the 26 month deprenyl-treated rats was largely due to difficulties in reversal—that is, in relearning the task after the position of the platform was changed. At 29 months, the deficits in the control group reflected a general retardation, indicated by an inability to solve the problem, and are indicative of severe cognitive impairment.

There is no obvious explanations for the results from the 26 month group, but it can't be ruled out that there is a possibility, however, of deprenyl producing a transient cognitive disruption. Very likely some period of time is required on the drug before the animals fully adjust to it. It could, however, be concluded from this data that the deficits were not permanent. To the contrary, the 29 month old animals on deprenyl showed significantly better learning than the controls.

When compared with saline-treated controls, the l-deprenyl treated rats survived longer, appeared healthier, showed more exploratory behavior, and less evidence of mental retardation at 29 months. Additionally, they did not lose as much body weight.

Finally, it should be emphasized that the data presented herein is with regard to rats as the exemplary mammal. It is known, however, that it is very likely that l-deprenyl will have similar effects in correlation in the human, primate, dog and cat brain. This is strengthened by strong known evidence that this exact parallel finding in humans with Parkinson's disease correlates precisely with similar findings in aged rats. Thus, the scientific correlation between the rat model and other mammals is known and recognized by those skilled in the art.

It therefore can be seen that this invention accomplishes at least all of its stated objectives.

What is claimed is:

1. A method of retarding age dependent weight loss in mammals, said method comprising:
    administering to the mammal a small but age dependent weight loss retarding effective amount of l-deprenyl or a pharmaceutically acceptable form thereof, at a frequency level of from one to seven times weekly, starting in middle age.

2. The method of claim 1 wherein the l-deprenyl is the levorotory optical isomer.

3. The method of claim 2 wherein the l-deprenyl is the hydrochloride addition salt form thereof.

4. The method of claim 1 wherein the addition level is at a level of from 0.01 mg/kg of body weight to 1.0 mg/kg of body weight.

5. The method of claim 4 wherein the addition level is from about 0.05 mg/kg of body weight to 0.5 mg/kg of body weight, dosed at least twice weekly starting in middle age.

6. The method of claim 1 wherein the mammal is a dog.

7. The method of claim 1 wherein the mammal is a cat.

* * * * *